(12) United States Patent
Han et al.

(10) Patent No.: US 12,246,051 B2
(45) Date of Patent: Mar. 11, 2025

(54) ***ASPERGILLUS ORYZAE* STRAIN AND USE THEREOF**

(71) Applicant: LG HOUSEHOLD & HEALTH CARE LTD., Seoul (KR)

(72) Inventors: Hyeong Min Han, Seoul (KR); Sunghwan Hwang, Seoul (KR); Sung Hun Youn, Seoul (KR); Seunggon Na, Seoul (KR); Sado Lee, Seoul (KR)

(73) Assignee: LG HOUSEHOLD & HEALTH CARE LTD., Seoul (KR)

( * ) Notice: Subject to any disclaimer, the term of this patent is extended or adjusted under 35 U.S.C. 154(b) by 0 days.

(21) Appl. No.: 18/325,252

(22) Filed: May 30, 2023

(65) Prior Publication Data

US 2023/0381258 A1 Nov. 30, 2023

(30) Foreign Application Priority Data

May 31, 2022 (KR) .................. 10-2022-0066545

(51) Int. Cl.
*A61K 36/258* (2006.01)
*A23L 31/00* (2016.01)
*A23L 33/105* (2016.01)
*A61K 36/062* (2006.01)
*C12N 1/14* (2006.01)
*C12R 1/69* (2006.01)

(52) U.S. Cl.
CPC ............ *A61K 36/258* (2013.01); *A23L 31/00* (2016.08); *A23L 33/105* (2016.08); *A61K 36/062* (2013.01); *C12N 1/145* (2021.05); *C12R 2001/69* (2021.05)

(58) Field of Classification Search
None
See application file for complete search history.

(56) References Cited

FOREIGN PATENT DOCUMENTS

| KR | 10-2018-0040784 A | | 4/2018 |
|---|---|---|---|
| KR | 20180040784 A | * | 4/2018 |
| KR | 10-2020-0000571 A | | 1/2020 |
| WO | WO-2023042959 A1 | * | 3/2023 |

* cited by examiner

*Primary Examiner* — Suzanne M Noakes
*Assistant Examiner* — Ciara A McKnight
(74) *Attorney, Agent, or Firm* — Birch, Stewart, Kolasch & Birch, LLP

(57) ABSTRACT

Provided are an *Aspergillus oryzae* LGYM4 strain; a red ginseng fermentation product including the strain or a fermentation product thereof; a food composition, a cosmetic composition, a quasi-drug composition, and a pharmaceutical composition, each including the red ginseng fermentation product; a method of preparing the red ginseng fermentation product, the method including the step of performing a fermentation by inoculating the strain into a composition including red ginseng; a red ginseng fermentation product prepared according to the preparation method; and a food composition, a cosmetic composition, a quasi-drug composition, and a pharmaceutical composition, each including the prepared red ginseng fermentation product.

9 Claims, No Drawings

Specification includes a Sequence Listing.

SEQUENCE LISTING

```
Sequence total quantity: 1
SEQ ID NO: 1           moltype = DNA  length = 560
FEATURE                Location/Qualifiers
misc_feature           1..560
                       note = Aspergillus oryzae LGYM4
source                 1..560
                       mol_type = genomic DNA
                       organism = unidentified
SEQUENCE: 1
attgatatgc ttaagttcag cgggtatccc tacctgatcc gaggtcaacc tggaaaaaga  60
ttgatttgcg ttcggcaagc gccggccggg cctacagagc gggtgacaaa gccccatacg  120
ctcgaggatc ggacgcggtg ccgccgctgc ctttggggcc cgtcccccc  ggagagggga  180
cgacgaccca acacacaagc cgtgcttgat gggcagcaat gacgctcgga caggcatgcc  240
ccccggaata ccaggggggcg caatgtgcgt tcaaagactc gatgattcac ggaattctgc  300
aattcacact agttatcgca tttcgctgcg ttcttcatcg atgccggaac caagagatcc  360
attgttgaaa gttttaactg attgcgatac aatcaactca gacttcacta gatcagacag  420
agttcgtggt gtctccggcg ggcgcgggcc cggggctgag agccccggc  ggccatgaat  480
ggcgggcccg ccgaagcaac taaggtacag taaacacggg tgggaggttg ggctcgctag  540
gaaccctaca ctcggtaatg                                              560
```

ASPERGILLUS ORYZAE STRAIN AND USE THEREOF

REFERENCE TO ELECTRONIC SEQUENCE LISTING

The application contains a Sequence Listing which has been submitted electronically in .XML format and is hereby incorporated by reference in its entirety. Said .XML copy, created on Mar. 15, 2023, is named "OPA23027.xml" and is 2,972 bytes in size. The sequence listing contained in this .XML file is part of the specification and is hereby incorporated by reference herein in its entirety.

BACKGROUND OF THE INVENTION

1. Field of the Invention

The present disclosure relates to an *Aspergillus oryzae* LGYM4 strain; a red ginseng fermentation product including the strain or a fermentation product thereof; a food composition, a cosmetic composition, a quasi-drug composition, and a pharmaceutical composition, each including the red ginseng fermentation product; a method of preparing the red ginseng fermentation product, the method including the step of performing a fermentation by inoculating the strain into a composition including red ginseng, a red ginseng fermentation product prepared according to the preparation method; and a food composition, a cosmetic composition, a quasi-drug composition, and a pharmaceutical composition, each including the prepared red ginseng fermentation product.

2. Description of the Related Art

Red ginseng is prepared by selecting 4-6 year-old Panax ginseng C. A. Meyer, which is a perennial herb belonging to the family Araliaceae, and then steaming and drying the same in an unpeeled state.

In oriental medicine, red ginseng is slightly warm in nature, sweet and slightly bitter in taste, and has been used as a representative herbal medicine that is effective in promoting health and preventing diseases, such as in replenishing energy and making the body fluid by entering the spleen, lungs, and heart.

During the process of steaming and drying red ginseng, active ingredients become more concentrated, and physiologically active ingredients effective for the human body, such as saponins, are produced, which help digestion and absorption, and improve the immune system and strengthen the functions.

Meanwhile, saponins are a kind of compounds chemically called glycosides. Saponins are found in the roots, stems, leaves, skins, and seeds of plants, etc., and are physiologically active substances effective for anticancer activity, antioxidant activity, and cholesterol lowering. Saponins in ginseng are called ginsenosides.

There are about 30 types of ginsenosides contained in red ginseng, and it is known that, among them, ginsenoside Rb1 is the most abundant, accounting for about 23% of the total saponins, followed by ginsenoside Rg1 accounting for about 19%, ginsenoside Re accounting for 15%, ginsenoside Rb2 accounting for 11%, ginsenoside Rc accounting for 12%, and ginsenoside Rd accounting for about 7%.

Among several types of ginsenosides, ginsenoside Rg3 is a component that is not found in ginseng and exists only in small amounts in red ginseng. Ginsenoside Rg3 inhibits thrombus formation and platelet aggregation, dilates blood vessels to promote blood circulation, and has the effect of lowering blood pressure. In addition, it inhibits the metastasis of cancer cells, inhibits the occurrence of resistance to anticancer drugs, and has strong effects on preventing dementia.

Of the two isomers of ginsenoside Rg3, the (R) type has been reported to have significantly superior immunity-increasing effect and antioxidant effect as compared to the (S) type, but a selective fermentation or synthesis method thereof is not yet known.

As a method of increasing the content of ginsenoside Rg3 in red ginseng, which is present in only a small amount in red ginseng, a method of using a red ginseng fermentation process (Korean Patent Publication No. 10-2018-0040784, Korean Patent Publication No. 10-2020-0000571), etc. has been suggested.

However, the above methods are merely to perform simple hypoglycosylation by deglycosylation of the entire unspecified ginsenosides through the red ginseng fermentation process. A method of selectively obtaining the (R) type ginsenoside Rg3 with superior effects is not disclosed.

In view of this background, the present inventors have discovered a novel *Aspergillus oryzae* strain, and they found that a red ginseng fermentation product prepared by inoculating the novel strain into a composition including red ginseng has an increased content of the (R) type ginsenoside Rg3, thereby completing the present disclosure.

SUMMARY OF THE INVENTION

An object of the present disclosure is to provide an *Aspergillus oryzae* LGYM4 strain.

Another object of the present disclosure is to provide a red ginseng fermentation product including the strain or a fermentation product thereof.

Still another object of the present disclosure is to provide a food composition including the red ginseng fermentation product.

Still another object of the present disclosure is to provide a cosmetic composition including the red ginseng fermentation product.

Still another object of the present disclosure is to provide a quasi-drug composition including the red ginseng fermentation product.

Still another object of the present disclosure is to provide a pharmaceutical composition including the red ginseng fermentation product.

Still another object of the present disclosure is to provide a method of preparing the red ginseng fermentation product, the method including the step of performing a fermentation by inoculating the strain into a composition including red ginseng.

Still another object of the present disclosure is to provide a red ginseng fermentation product prepared by the preparation method.

Still another object of the present disclosure is to provide a food composition including the prepared red ginseng fermentation product.

Still another object of the present disclosure is to provide a cosmetic composition including the prepared red ginseng fermentation product.

Still another object of the present disclosure is to provide a quasi-drug composition including the prepared red ginseng fermentation product.

Still another object of the present disclosure is to provide a pharmaceutical composition including the prepared red ginseng fermentation product.

DETAILED DESCRIPTION OF THE PREFERRED EMBODIMENTS

The present disclosure will be described in detail as follows. Meanwhile, each description and embodiment disclosed in this disclosure may also be applied to other descriptions and embodiments. That is, all combinations of various elements disclosed in this disclosure fall within the scope of the present disclosure. Further, the scope of the present disclosure is not limited by the specific description described below.

In the present disclosure, a novel *Aspergillus oryzae* LGYM4 strain has been discovered, and it was newly demonstrated that a red ginseng fermentation product prepared by inoculating the novel strain into a composition including red ginseng has an increased content of the (R) type ginsenoside Rg3.

An aspect of the present disclosure provides an *Aspergillus oryzae* LGYM4 strain deposited with Accession No. KCTC 14533BP.

As used herein, the term "*Aspergillus oryzae*" is known as Hwangguk, and is a representative strain of nuruk mold used in the preparation of rice wine, Japanese-style soybean paste, and soy sauces. The colony is initially white, and then it turns from yellowish to yellowish green as conidia form, and becomes brown when old. It is known to have strong starch saccharification and protein decomposition properties.

The present inventors have developed a novel strain belonging to the *Aspergillus oryzae*, and named *Aspergillus oryzae* LGYM4, and deposited with Accession No. KCTC 14533BP.

In one specific embodiment, the strain may have a ginsenoside bioconversion activity.

As used herein, the term "ginsenoside" refers to a saponin component that contains the main physiologically active components of ginseng. Among the ginsenosides, Re, Rg1, Rb1, Rc, Rb2, Rf, and Rd are major ginsenosides that account for 90% or more of the total saponins, and show a very poor absorption rate in the living body due to their large size.

On the other hand, minor ginsenosides consist of Rg2, Rh1, Rg6, F2, Rk3, Rh4, and Rg3. Recently, research results related to the excellent pharmacological efficacy of minor ginsenosides have been published. Hence, research on methods for bioconversion of major ginsenosides into minor ginsenosides with excellent physiological activity has attracted attention.

As used herein, the term "bioconversion" refers to a method of producing a desired product from a precursor by using enzymatic functions possessed by microorganisms. The bioconversion induces structural changes in materials through biological methods such as microbial fermentation or enzyme treatment, etc. Due to the change, the content of the active ingredient is increased or the absorption rate is improved, and new functional ingredients are created. This bioconversion technology is widely used for the production of useful substances such as amino acids and vitamins as well as the production of pharmaceuticals including antibiotics and steroids and pharmaceutical raw materials.

In one embodiment of the present disclosure, it was confirmed that the *Aspergillus oryzae* LGYM4 strain has the bioconversion activity of major ginsenosides into minor ginsenosides, and the *Aspergillus oryzae* LGYM4 strain increases the content of minor ginsenosides in the total ginsenosides by bioconversion of major ginsenosides, thereby enhancing physiological activity, and in particular, it selectively increases the content of a specific minor ginsenoside ((R) type ginsenoside Rg3) having high physiological activity among minor ginsenosides (Example 3).

Another aspect of the present disclosure provides a red ginseng fermentation product including the strain or a fermentation product thereof.

With respect to the objects of the present disclosure, the strain refers to the novel *Aspergillus oryzae* LGYM4 strain.

As used herein, the term "fermentation" refers to a process in which microorganisms break down organic materials using their own enzymes, excluding putrefaction. Fermentation and putrefaction proceed by similar processes, but when useful substances are produced as a result of decomposition, it is called fermentation, and when bad smells or harmful substances are produced, it is called putrefaction.

As used herein, the term "fermentation product" includes not only a fermented material itself, but also all types of materials including the fermentation product generated from the strain, such as a culture medium of a strain in which the strain and the culture coexist, a fermentation product obtained by filtering the strain from the culture medium, a fermentation product obtained by sterilizing the strain from the culture medium and filtering the same, an extract obtained by extracting the fermentation product or the culture medium including the same, a dilution obtained by diluting the fermentation product or the extract thereof, a dried product obtained by drying the fermentation product or the extract thereof, a lysate obtained by collecting and disrupting cells of the strain, etc. In addition to all types of materials including the fermentation product, dilutions of all types of materials including the fermentation product, concentrates thereof, crude refined products thereof, and refined products thereof are included.

As used herein, the terms "concentrate", "culture medium", and "lysate", which are produced resulting from decomposition of organic compounds by microorganisms, may be used interchangeably with the fermentation product.

As used herein, the term "red ginseng fermentation product" includes all of a red ginseng fermentation product, a concentrate of the red ginseng fermentation product, or a fermentation product of a red ginseng concentrate, etc.

Specifically, in the present disclosure, the red ginseng fermentation product may include i) a fermentation product obtained by fermentation of red ginseng by the novel *Aspergillus oryzae* LGYM4 strain, ii) a product obtained by inoculating the novel *Aspergillus oryzae* LGYM4 strain into a composition including a red ginseng extract, a concentrate of the red ginseng extract, or red ginseng, iii) a fermentation product of ii), or iv) a concentrate of i) to iii), but is not limited thereto.

In the present disclosure, a method of obtaining the fermentation product from the strain is not particularly limited, and the fermentation product may be obtained according to a method commonly used in the related art or similar art.

In the present disclosure, a fermentation process of obtaining the fermentation product may be fermentation by treating the separated strain with sugar, which is an energy source of the strain, but the temperature of the fermentation process and the fermentation time are not particularly limited, and may be variously selected according to fermentation precursor materials, fermentation conditions, the type of materials to be obtained from the fermentation product, etc.

For example, it may be performed at a temperature of 20° C. to 40° C., specifically 30° C. to 40° C., more specifically about 37° C. In addition, for example, it may be fermented for 1 day to 10 days, specifically for 1 day to 5 days, and more specifically for a period of about 2 days, but is not limited thereto.

In the present disclosure, the red ginseng fermentation product may have an increased content of the (R) type ginsenoside Rg3, specifically, an increased value, the value obtained by dividing the content of the (R) type ginsenoside Rg3 by the content of the (S) type ginsenoside Rg3, as compared to that before fermentation. Specifically, as used herein, the term "(R) type ginsenoside Rg3/(S) type ginsenoside Rg3 value" refers to a value showing the content ratio of the (R) type and the (S) type which are two isomers of ginsenoside Rg3, and may be expressed as "R/S value". For example, when the R/S value is increased, as compared to that before fermentation, it means that the (R) type is selectively increased, as compared to the (S) type.

As used herein, "the increased content of the (R) type ginsenoside Rg3" means that the content of the (R) type ginsenoside Rg3 is increased, as compared to that of the composition including red ginseng, which is not subjected to fermentation.

In one embodiment of the present disclosure, it was confirmed that the red ginseng fermentation product showing a selective increase in the content of the (R) type ginsenoside Rg3 and in the (R) type ginsenoside Rg3/(S) type ginsenoside Rg3 value may be prepared by using the novel *Aspergillus oryzae* LGYM4 strain (Example 3).

Still another aspect of the present disclosure provides a food composition including the red ginseng fermentation product.

The red ginseng fermentation product is the same as described above.

As used herein, the term "food" refers to meat, sausage, bread, chocolate, candy, snacks, confectionery, pizza, ramen, other noodles, chewing gums, dairy products including ice cream, various soups, beverages, tea, drinks, alcoholic beverages and vitamins complex, health functional foods and health foods, etc., and include all foods in the usual sense.

The health functional food refers to a food prepared and processed using raw materials or ingredients having useful functions for the human body. In particular, the term 'functional' means to obtain a useful effect for health purposes such as nutrient control or physiological action on the structure and function of the human body. The food of the present disclosure may be prepared by methods commonly used in the art. In the preparation, the food may be prepared by adding raw materials and components commonly added in the art. In addition, the formulation of the food may be prepared without limitation as long as the formulation is recognized as a food. The food composition of the present disclosure may be prepared in various forms of formulation. The food has the advantage that, unlike a general medicine, there is no side effect that may occur when taking the medicine for a long time. Due to its high portability, the food of the present disclosure may be taken as supplements to enhance the effectiveness of immune enhancement.

The health food refers to a type of food that possesses active health maintenance or promotion effects, as compared to typical foods, and the health supplement food refers to a type of food that is consumed for health supplementation purposes. In some cases, the terms "health functional food", "health food", and "health supplement food" are used interchangeably.

Specifically, the health functional food is a type of food prepared by adding the red ginseng fermentation product to a food material such as beverages, teas, spices, gum or confectioneries, or prepared in the form of a capsule, a powder, or a suspension. When ingested, the health functional food has a specific effect on health, yet it contains food as a raw material, unlike typical drugs, and therefore has an advantage of not having side effects which may arise from long-term use of the drug.

The food composition of the present disclosure is very useful, as it may be ingested on a daily basis, and is expected to provide a high immunity enhancing effect.

The composition may further include a physiologically acceptable carrier, and the type of carrier is not particularly limited, and thus any carrier may be used, as long as it is commonly used in the art.

In addition, the composition may include additional components that may enhance smell, taste, or visual appearance, which are generally used in a food composition. For example, the composition may include vitamin A, C, D, E, B1, B2, B6 or B12, niacin, biotin, folate, or pantothenic acid, etc. In addition, the composition may include minerals such as zinc (Zn), iron (Fe), calcium (Ca), chromium (Cr), magnesium (Mg), manganese (Mn), copper (Cu), chromium (Cr), etc. In addition, the composition may include amino acids such as lysine, tryptophan, cysteine, valine, etc.

In addition, the composition may include food additives such as a preservative (potassium sorbate, sodium benzoate, salicylic acid, sodium dehydroacetate, etc.), a sterilizer (bleaching powder, high-grade bleaching powder, sodium hypochlorite, etc.), an antioxidant (butyl hydroxyanisole (BHA), butyl hydroxytoluene (BHT), etc.), a dye (tar pigment, etc.), a coloring agent (sodium nitride, sodium nitrate, etc.), a bleaching agent (sodium sulfate), a flavor enhancer (MSG, monosodium glutamate, etc.,), a sweetener (dulcin, cyclamate, saccharin, sodium, etc.), a spice (vanillin, lactone, etc.), a swelling agent (alum, potassium D-bitartrate, etc.), a reinforcing agent, an emulsifier, a thickening agent (paste), a coating agent, a gum base agent, a foam inhibitor, a solvent, an improving agent, etc. The additives may be selected according to the type of food and may be used in an appropriate amount.

The red ginseng fermentation product may be added as-is or together with other foods or food components, and may be appropriately used according to a common method. A mixed amount of the active ingredients may be suitably determined according to the intended use (preventive, health, or therapeutic purposes). Generally, the food composition of the present disclosure may be added in an amount of 50 parts by weight or less, specifically, 20 parts by weight of less with respect to a food or drink, upon preparing the food or drink. However, when consumed for a long period of time for health and sanitary purposes, the composition may be used in an amount below the range. In addition, the active ingredients may be used in an amount above the range, because the active ingredient carries no safety risk.

The food composition of the present disclosure may be used as, for example, a health beverage composition. In this case, the health beverage composition may include additional components such as various flavoring agents or natural carbohydrates, etc., like common beverages. The above-described natural carbohydrates may include monosaccharides such as glucose and fructose; disaccharides such as maltose and sucrose; polysaccharides such as dextrin and cyclodextrin; sugar alcohols such as xylitol, sorbitol, erythritol, etc. As a sweetening agent, a natural sweetening agent such as thaumatin or stevia extract; a synthetic sweetening agent such as saccharin and aspartame, etc. may be used. A proportion of the natural carbohydrate is generally in a range of about 2 g to about 10 g, specifically, about 4 g to 8 g per 100 mL of the composition of the present disclosure.

In addition, the health beverage composition may further include various nutritional supplements, vitamins, electrolytes, flavorings, coloring agents, pectic acid and salts thereof, alginic acid and salts thereof, organic acids, protective-colloidal thickeners, pH regulators, stabilizers, preservatives, glycerin, alcohols or carbonating agents, etc. Furthermore, the health beverage composition may include fruit flesh used for natural fruit juices, fruit juice drinks, or vegetable drinks. These components may be used alone or in combination thereof. A ratio of these additives may not be important, but it is generally selected in the range of 0.01 part by weight to 0.1 part by weight per 100 parts by weight of the composition of the present disclosure.

In the food composition of the present disclosure, the red ginseng fermentation product may be included in an amount of 0.001% to 90%, specifically 0.01% to 30%, more specifically 0.05% to 10%, much more specifically 0.05% to 0.15%, based on the total weight of the food composition.

Still another aspect of the present disclosure provides a cosmetic composition including the red ginseng fermentation product.

The red ginseng fermentation product is the same as described above.

In the cosmetic composition of the present disclosure, the red ginseng fermentation product may be included in an amount of 0.001% to 90%, specifically 0.01% to 30%, more specifically 0.05% to 10%, much more specifically 0.05% to 0.15%, based on the total weight of the cosmetic composition, but is not limited thereto.

The cosmetic composition of the present disclosure may have a formulation selected from the group consisting of solutions, external ointments, creams, foams, nourishing lotions, softening lotions, perfume, packs, soft water, emulsions, makeup bases, essences, soaps, liquid cleansers, bath preparations, sunscreen creams, sun oils, suspensions, emulsions, pastes, gels, lotions, powders, soaps, surfactant-containing cleansing agents, oils, powder foundations, emulsion foundations, wax foundations, patches, and sprays, but is not limited thereto.

The cosmetic composition of the present disclosure may further include one or more cosmetically acceptable carriers blended in general skin cosmetics, and as common ingredients, for example, oil, water, a surfactant, a humectant, lower alcohol, a thickener, a chelating agent, a colorant, a preservative, a fragrance, etc. may be appropriately blended, but is not limited thereto.

The cosmetically acceptable carrier included in the cosmetic composition of the present disclosure may vary according to the formulation of the cosmetic composition.

When the cosmetic formulation of the present disclosure is an ointment, a paste, a cream, or a gel, animal oil, vegetable oil, wax, paraffin, starch, tragacanth, a cellulose derivative, polyethylene glycol, silicon, bentonite, silica, talc, zinc oxide, etc., may be used as the carrier ingredient, but is not limited thereto. These compounds may be used alone or in a mixture of two or more thereof.

When the formulation of the present disclosure is a solution or an emulsion, a solvent, a solubilizing agent, an emulsifying agent, etc. may be used as the carrier ingredient. For example, water, ethanol, isopropanol, ethyl carbonate, ethyl acetate, benzyl alcohol, benzyl benzoate, propylene glycol, 1,3-butyl glycol oil, etc. may be used. In particular, cottonseed oil, peanut oil, corn seed oil, olive oil, castor oil, sesame oil, glycerol fatty acid ester, or polyethylene glycol or sorbitan fatty acid ester may be used, but is not limited thereto. These compounds may be used alone or in combination of two or more thereof.

When the formulation of the present disclosure is a suspension, a liquid diluent such as water, ethanol, or propylene glycol, a suspending agent such as ethoxylated isostearyl alcohol, polyoxyethylene sorbitol ester, or polyoxyethylene sorbitan ester, microcrystalline cellulose, aluminum methahydroxide, bentonite, agar, tragacanth, etc., may be used as the carrier ingredient, but is not limited thereto. These compounds may be used alone or in combination of two or more thereof.

When the formulation of the present disclosure is a soap, an alkali metal salt of a fatty acid, a fatty acid hemiester salt, a fatty acid protein hydrolysate, isethionate, a lanolin derivative, a fatty alcohol, vegetable oil, glycerol, sugar, etc. may be used as the carrier ingredient, but is not limited thereto. These compounds may be used alone or in combination of two or more thereof.

When the formulation of the present disclosure is a powder or spray, lactose, talc, silica, aluminum hydroxide, calcium silicate, polyamide powder, or a composition thereof may be used as the carrier ingredient. In particular, in the case of a spray, the composition may further include a propellant such as a chlorofluorohydrocarbon, propane/butane, or dimethyl ether.

On the other hand, all ingredients described in the present disclosure may be preferably included in the composition of the present disclosure within the range that does not exceed the maximum allowable usage specified in the regulations on cosmetic safety standards and China's 'cosmetic safety and technical standard'.

Still another aspect of the present disclosure provides a quasi-drug composition including the red ginseng fermentation product.

The red ginseng fermentation product is the same as described above.

As used herein, the term "quasi-drug" may be selected from the group consisting of body cleansers, disinfectant cleaners, detergents, detergents for kitchen, detergents for cleaning, toothpaste, mouth wash, wet wipes, detergents, soaps, hand wash, hair cleaners, hair softeners, humidifier fillers, masks, ointments, and filter filler, but is not limited thereto.

The quasi-drug composition of the present disclosure may further include a pharmaceutically acceptable carrier, excipient, or diluent, as needed, in addition to the ingredients above. The pharmaceutically acceptable carrier, excipient, or diluent is not limited as long as it does not impair the effects of the present disclosure, and examples thereof may include fillers, extenders, binders, wetting agents, disintegrants, surfactants, lubricants, sweeteners, fragrances, preservatives, etc.

Representative examples of the pharmaceutically acceptable carrier, excipient, or diluent of the present disclosure may include lactose, dextrose, sucrose, sorbitol, mannitol, xylitol, maltitol, starch, gelatin, glycerin, gum acacia, alginate, calcium phosphate, calcium carbonate, calcium silicate, cellulose, methyl cellulose, microcrystalline cellulose, polyvinyl pyrrolidone, water, methylhydroxybenzoate, propylhydroxybenzoate, talc, magnesium stearate, mineral oil, propylene glycol, polyethylene glycol, vegetable oil, injectable esters, Witepsol, Macrogol, Tween 61, cacao butter, laurin butter, etc.

When the red ginseng fermentation product of the present disclosure is used as a quasi-drug, one or more active ingredients exhibiting the same or similar function may be further included.

The quasi-drug composition of the present disclosure may further include an active ingredient known in the art. The additional ingredient may be included in an amount of 0.0001% by weight to 10% by weight with respect to the total weight of the composition. The content range may be adjusted according to requirements, such as ease of formulation of the red ginseng fermentation product of the present disclosure.

The formulation methods, doses, usages, components, etc. of quasi-drugs may be appropriately selected from common techniques known in the art.

Still another aspect of the present disclosure provides a pharmaceutical composition including the red ginseng fermentation product.

The red ginseng fermentation product is the same as described above.

The pharmaceutical composition of the present disclosure may further include a pharmaceutically acceptable carrier, excipient, or diluent commonly used in the preparation of pharmaceutical compositions, and the carrier may include a non-naturally occurring carrier. The carrier, excipient, and diluent may include lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate, and mineral oil.

Further, the pharmaceutical composition may be used after being formulated into a tablet, a pill, a powder, granules, a capsule, a suspension, a solution for internal use, an emulsion, a syrup, a sterilized aqueous solution, a non-aqueous solvent, a suspension, an emulsion, a freeze-dried preparation, a transdermal patch, a gel, a lotion, an ointment, a cream, a patch, a cataplasma, a paste, a spray, a skin emulsion, a skin suspension, a transdermal delivery patch, a drug-containing bandage, or a suppository, according to each common method.

Specifically, when formulated, it may be prepared using diluents or excipients, such as fillers, extenders, binders, wetting agents, disintegrants, surfactants, etc. commonly used. Solid formulations for oral administration include, but are not limited to, tablets, pills, powders, granules, capsules, etc. Such solid formulations may be prepared by mixing with at least one or more excipients, for example, starch, calcium carbonate, sucrose, lactose, gelatin, etc. In addition to simple excipients, lubricants such as magnesium stearate and talc may also be used. Liquid formulations for oral administration may be prepared by adding various excipients, for example, wetting agents, flavoring agents, aromatics, preservatives, etc., in addition to water and liquid paraffin. Formulations for parenteral administration may include sterilized aqueous solutions, non-aqueous solutions, suspensions, emulsions, lyophilized preparations, and suppositories. As non-aqueous solvents or suspending agents, propylene glycol, polyethylene glycol, plant oils such as olive oil, injectable esters such as ethyl oleate, etc. may be used. As the base of the suppositories, witepsol, Macrogol, Tween 61, cacao butter, laurin butter, glycerogelatin, etc. may be used.

In the pharmaceutical composition of the present disclosure, the red ginseng fermentation product may be included in an amount of 0.001% to 90%, specifically 0.01% to 30%, more specifically 0.05% to 10%, much more specifically 0.05% to 0.15%, based on the total weight of the pharmaceutical composition, but is not limited thereto.

The pharmaceutical composition of the present disclosure may be administered in a pharmaceutically effective amount. As used herein, the term "pharmaceutically effective amount" refers to an amount which is sufficient to treat diseases at a reasonable benefit/risk ratio applicable to any medical treatment. The effective dosage level may be determined according to factors, which include the type of a subject and severity, age, sex, drug activity, sensitivity to drug, administration time, administration route and excretion rate, duration of treatment, and other drugs used simultaneously, and other factors well known in the medical field. For example, the pharmaceutical composition may be administered at a dose of 0.01 mg/kg to 500 mg/kg per day, specifically, 10 mg/kg to 100 mg/kg per day, and the administration may be administered once a day or divided several times.

The pharmaceutical composition may be administered as an individual therapeutic agent or in combination with other therapeutic agents, and may be administered sequentially or simultaneously with an existing therapeutic agent. In addition, it may be administered in a single dose or multiple doses. It is important to administer an amount that will achieve the maximum effect with a minimum amount without side effects, with taking all of the above factors into consideration. The amount may be readily determined by those skilled in the art.

Depending on the method as desired, the pharmaceutical composition may be administered orally or parenterally (e.g., intravenously, subcutaneously, intraperitoneally or topically). Dosage may vary according to a patient's conditions and body weight, severity of disease, drug formulation, administration route and time, but may be appropriately selected by those skilled in the art.

Still another aspect of the present disclosure provides a method of preparing the red ginseng fermentation product, the method including the step of performing a fermentation by inoculating the strain into a composition including red ginseng.

Specifically, in the present disclosure, the step of performing a fermentation may be performing a fermentation after adding the strain culture broth to the composition including red ginseng, but is not limited thereto. It may be applied to any of red ginseng, wild ginseng, ginseng, fresh ginseng, white ginseng, red ginseng tail root, ginseng tail root, wood-cultivated ginseng, mountain-cultivated ginseng, ginseng tail root, original ginseng, and taegeuk ginseng which are processed into various forms.

As used herein, the term "ginseng" refers to a shade perennial plant that belongs to the family Araliaceae in the order Apiales, in terms of plant taxonomy. In addition, ginseng not treated to make red ginseng is referred to as "fresh ginseng". Ginseng is a broadest term that encompasses various types such as wild ginseng, fresh ginseng, white ginseng, red ginseng tail root, ginseng tail root, wood-cultivated ginseng, mountain-cultivated ginseng, ginseng tail root, original ginseng, and taegeuk ginseng. Ginseng is characterized by having a low content of ginsenoside Rg3, as compared to red ginseng.

More specifically, the preparation method of the present disclosure may include the step of adding the novel *Aspergillus oryzae* LGYM4 strain of the present disclosure to the composition including red ginseng, but is not limited thereto.

The temperature, fermentation time, etc. in the fermentation step are not particularly limited, and may be variously selected according to fermentation precursor materials, fermentation conditions, the type of a material to be obtained from the fermentation product, etc.

The fermentation may be performed, for example, at 20° C. to 40° C., specifically at 30° C. to 40° C., more specifically around 37° C. In addition, the fermentation may be performed, for example, for 1 day to 10 days, specifically, for 1 day to 5 days, and more specifically, for a period of about 2 days, but is not limited thereto.

The preparation method of the present disclosure may further include the step of filtering the prepared red ginseng fermentation product.

Further, the preparation method of the present disclosure may further include the step of concentrating.

In the present disclosure, the filtration method and concentration method are not particularly limited, and may be appropriately selected by those skilled in the art.

In the present disclosure, the prepared red ginseng fermentation product may have an increased content of the (R) type ginsenoside Rg3, specifically, an increased (R) type ginsenoside Rg3/(S) type ginsenoside Rg3 value, as compared to the composition including red ginseng before fermentation.

In the present disclosure, "the increased content of the (R) type ginsenoside Rg3" means that the content of the (R) type ginsenoside Rg3 is increased, as compared to that of the composition including red ginseng, which is not subjected to fermentation.

In one embodiment of the present disclosure, it was confirmed that the red ginseng fermentation product showing a selective increase in the content of the (R) type ginsenoside Rg3 and in the (R) type ginsenoside Rg3/(S) type ginsenoside Rg3 value may be prepared by using the novel *Aspergillus oryzae* LGYM4 strain (Example 3).

Still another aspect of the present disclosure provides a red ginseng fermentation product prepared according to the preparation method.

The preparation method and the red ginseng fermentation product are the same as described above.

Still another aspect of the present disclosure provides a food composition including the prepared red ginseng fermentation product.

The food composition, the red ginseng fermentation product, and the preparation method thereof are the same as described above.

Still another aspect of the present disclosure provides a cosmetic composition including the prepared red ginseng fermentation product.

The cosmetic composition, the red ginseng fermentation product, and the preparation method thereof are the same as described above.

Still another aspect of the present disclosure provides a quasi-drug composition including the prepared red ginseng fermentation product.

The quasi-drug composition, the red ginseng fermentation product, and the preparation method thereof are the same as described above.

Still another aspect of the present disclosure provides a pharmaceutical composition including the prepared red ginseng fermentation product.

The pharmaceutical composition, the red ginseng fermentation product, and the preparation method thereof are the same as described above.

Hereinafter, the present disclosure will be described in more detail with reference to exemplary embodiments. However, these exemplary embodiments are only for illustrating the present disclosure, and the scope of the present disclosure is not intended to be limited by these exemplary embodiments.

Example 1: Identification of Novel Strain

An *Aspergillus oryzae* strain capable of selectively increasing the content of the (R) type ginsenoside Rg3 by bioconversion of major ginsenosides was selected.

In detail, microorganisms were identified from a medicinal nuruk, and 24 kinds of strains were identified and then separated. From 24 kinds of the separated strains, 5 kinds of strains (YM4, BS1, BS2, BS4, BS5) appliable to foods were selected again, and it was evaluated whether or not they selectively increase the content of the (R) type ginsenoside Rg3. More specifically, 5 kinds of the selected strains were cultured in a PDB liquid medium for 1 day under environments of 180 rpm and 30° C., respectively, followed by subculture in a 40% (W/V) red ginseng medium (red ginseng concentrate 400 g+PBS total 1 L) at a ratio of 1:10 for 1 day. The red ginseng concentrate used in the red ginseng medium was purchased from Daedong Korea Ginseng Co., Ltd. Subsequently, the strains were cultured for 2 days under environments of 180 rpm and 30° C., respectively, and then sterilized in a water bath at 90° C. through 1 h incubation. After sterilization, filtration was performed using a microfilter, and the content of ginsenosides was quantified through LC/Q-TOF. The results are shown in Table 1 below.

TABLE 1

| Section | Ginsenoside content (mg/g) | | | | | | | | | |
|---|---|---|---|---|---|---|---|---|---|---|
| | Rb1 | Rb2 | Rc | Rb3 | Re | Rd | Ro | Rg1 | Rg2 (S) | Rg2 (R) |
| Before fermentation | 18.95 | 15.75 | 8.8 | 7.9 | 5.525 | 3.8 | 2.625 | 3.625 | 1.8 | 0.6 |
| YM4 | 17.95 | 1.5 | 8.55 | 7.725 | 4.8 | 36.5 | 2.225 | 3.15 | 1.875 | 0.7 |
| BS1 | 18.325 | 1.525 | 8.5 | 7.675 | 5.15 | 3.85 | 2.3 | 3.25 | 1.85 | 0.675 |
| BS2 | 17.9 | 1.375 | 8.35 | 7.475 | 4.85 | 3.775 | 2.275 | 3.15 | 1.875 | 0.675 |
| BS4 | 18.175 | 1.5 | 8.475 | 7.65 | 5.05 | 3.8 | 2.475 | 3.275 | 1.85 | 0.675 |
| BS5 | 16.85 | 1.4 | 7.925 | 7.2 | 4.675 | 3.55 | 1.725 | 3 | 1.725 | 0.6 |

| Section | Ginsenoside content (mg/g) | | | | | | | |
|---|---|---|---|---|---|---|---|---|
| | Rg6 | Rg3 (S) | Rg3 (R) | Rk1 | Rg5 | F4 | Rh1 (S) | Rh1 (R) | Rh4 |
| Before fermentation | 0.7 | 2.325 | 1.15 | 1.7 | 4 | 1.525 | 0.775 | 0.45 | 0.8 |
| YM4 | 0.75 | 2.525 | 2.1 | 1.75 | 3.975 | 1.575 | 0.825 | 0.525 | 0.875 |

TABLE 1-continued

| | | | | | | | | | |
|---|---|---|---|---|---|---|---|---|---|
| BS1 | 0.725 | 2.5 | 1.25 | 1.75 | 3.95 | 1.6 | 0.825 | 0.5 | 0.85 |
| BS2 | 0.7 | 2.425 | 1.225 | 1.75 | 3.85 | 1.575 | 0.85 | 0.525 | 0.825 |
| BS4 | 0.7 | 2.45 | 1.25 | 1.7 | 3.75 | 1.575 | 0.825 | 0.5 | 0.825 |
| BS5 | 0.675 | 2.275 | 1.125 | 1.575 | 3.55 | 1.425 | 0.775 | 0.475 | 0.775 |

As shown in Table 1, it was confirmed that the red ginseng medium fermented with YM4 showed a remarkable increase in the content of the (R) type ginsenoside Rg3, as compared to those fermented with other strains, and showed an 82% increase, as compared to that before fermentation. YM4 was selected as a strain having the excellent efficacy capable of selectively increasing the content of the (R) type ginsenoside Rg3.

The following ITS sequence of the selected YM4 strain was subjected to NCBI blast analysis, and as a result, the strain has 97.69% to 99.82% identity to the existing strains, and it was confirmed that the separated strain is a different strain from the existing strains.

ITS sequence of LGYM4 strain (SEQ ID NO: 1):
ATTGATATGCTTAAGTTCAGCGGGTATCCCTACCTGATCCGAGGTCAAC

CTGGAAAAGATTGATTTGCGTTCGGCAAGCGCCGGCCGGGCCTACAGA

GCGGGTGACAAAGCCCCATACGCTCGAGGATCGGACGCGGTGCCGCGC

TGCCTTTGGGGCCCGTCCCCCCCGGAGAGGGGACGACGACCCAACACAC

AAGCCGTGCTTGATGGGCAGCAATGACGCTCGGACAGGCATGCCCCCG

GAATACCAGGGGGCGCAATGTGCGTTCAAAGACTCGATGATTCACGGAA

TTCTGCAATTCACACTAGTTATCGCATTTCGCTGCGTTCTTCATCGATG

CCGGAACCAAGAGATCCATTGTTGAAAGTTTTAACTGATTGCGATACAA

TCAACTCAGACTTCACTAGATCAGACAGAGTTCGTGGTGTCTCCGGGGG

GGGGGGCCCGGGGCTGAGAGCCCCCGGCGGCCATGAATGGCGGGCCCG

CCGAAGCAACTAAGGTACAGTAAACACGGGTGGGAGGTTGGGCTCGCTA

GGAACCCTACACTCGGTAATG

In addition, as a result of comparing the gene sequence with that of the *Aspergillus oryzae* strain (NCBI GenBank accession number: NR_135395.1), which corresponds to a known strain, YM4 shows 99.82% identity, and thus it was also confirmed that the strain discovered in Example 1 is a novel strain different from the known strain.

The new strain (YM4) was named *Aspergillus oryzae* LGYM4, and was deposited at Korean Collection for Type Cultures (KCTC), Korea Research Institute of Bioscience and Biotechnology, an international depository under the Budapest Treaty, on Apr. 12, 2021 with Accession No. KCTC 14533BP.

Example 2: Preparation of Red Ginseng Fermentation Product

Comparative Example 4 kg of red ginseng extract and 4 kg of purified water were introduced into a fermentor, and dissolved at about 25 Brix, and sterilized at 121° C. for 30 minutes to prepare an unfermented red ginseng extract, which was used as a comparative example.

Example

A medium containing 3% whole wheat flour, 0.3% yeast extract, 0.1% monobasic potassium phosphate, and 0.05% magnesium sulfate was sterilized at 121° C. for 30 minutes, and then *Aspergillus oryzae* LGYM4 strain selected in Example 1 was inoculated and cultured under environments of 160 rpm, 37° for 2 days to prepare a seed culture.

Meanwhile, 4 kg of red ginseng extract and 4 kg of purified water were introduced into the fermentor, and dissolved at about 25 Brix, and then sterilized at 121° C. for 30 minutes to prepare an experimental group.

After sterilization, the fermentor was cooled to 37° C., and 1.2 L of the seed culture was inoculated into the experimental group and cultured for 1 day under environments of 37° C., 150 rpm, 0.5 vvm, 0.6 bar to prepare a red ginseng fermentation product.

Then, the product was sterilized again at 95° C. for 1 hour, and then a filtered fermentation broth, from which impurities were removed, was obtained by filtration using diatomaceous earth.

Subsequently, in order to recover ginsenosides adsorbed onto diatomaceous earth, 50% (v/v) of 95% alcohol with respect to a liquid volume was added and washed to obtain alcohol containing the adsorbed ginsenosides.

Subsequently, the filtered fermentation broth and the alcohol containing the adsorbed ginsenoside were mixed (2:1) and concentrated to 67 Brix or higher, and then sterilized through heat treatment at 95° C. for 1 hour to obtain a concentrate of the red ginseng fermentation product.

Example 3: Ginsenoside Analysis of Red Ginseng Fermentation Product

In order to measure the content of the ginsenoside components contained in the red ginseng fermentation product prepared in Example 2, high performance liquid chromatography (HPLC, Agilent) was used. The results are shown in Table 2 below. The ginsenoside concentrations of the red ginseng extract, the red ginseng fermentation product, and the red ginseng fermentation product concentrate were calculated as a value, which was converted based on the solid content of 72%, and compared at the same concentration (brix) level.

TABLE 2

| | Red ginseng extract | Red ginseng fermentation product | Red ginseng fermentation product concentrate |
|---|---|---|---|
| Rg3(S) (mg/g) | 2.97 | 11.43 | 11.60 |
| Rg3(R) (mg/g) | 1.79 | 8.81 | 8.72 |
| Ratio (R/S) | 60.27% | 77.08% | 75.17% |

As shown in Table 2, as a result of ginsenoside analysis of the red ginseng fermentation product, it was confirmed that the content of the (R) type ginsenoside Rg3 was 8.81 mg/g, indicating 492% increase, as compared to that of the red ginseng extract before fermentation. In addition, when the content ratio of (R) type and (S) type, which are two isomers of ginsenoside Rg3, was examined, the R/S value of the red ginseng extract before fermentation was 60.27%, whereas the R/S value of the red ginseng fermentation product was 77.08%, indicating that the (R) type was selectively increased, as compared to the (S) type.

In addition, as a result of ginsenoside analysis of the red ginseng fermentation product concentrate, the content of the (R) type ginsenoside Rg3 was 8.72 mg/g, indicating 487% increase, as compared to that of the red ginseng extract before fermentation. In addition, when the content ratio of (R) type and (S) type, which are two isomers of ginsenoside Rg3, was examined, the R/S value of the red ginseng extract before fermentation was 60.27%, whereas the R/S value of the red ginseng fermentation product concentrate was 75.17%, indicating that the (R) type was selectively increased, as compared to the (S) type.

Through these results, it was confirmed that the novel strain of the present disclosure may increase the physiological activity by increasing the content of minor ginsenosides among the total ginsenosides through bioconversion of major ginsenosides, and in particular, the novel strain has an excellent efficacy of selectively increasing the content of a specific minor ginsenoside ((R) type ginsenoside Rg3) with high physiological activity among minor ginsenosides. Accordingly, it was confirmed that the red ginseng fermentation product showing the selective increase in the (R) type ginsenoside Rg3 content and in the (R) type ginsenoside Rg3/(S) type ginsenoside Rg3 value may be prepared by the method of preparing the red ginseng fermentation product using the novel strain of the present disclosure.

Based on the above description, it will be understood by those skilled in the art that the present disclosure may be implemented in a different specific form without changing the technical spirit or essential characteristics thereof. In this regard, it should be understood that the above embodiment is not imitative, but illustrative in all aspects. The scope of the disclosure is defined by the appended claims rather than by the description preceding them, and therefore all changes and modifications that fall within metes and bounds of the claims, or equivalents of such metes and bounds are therefore intended to be embraced by the claims.

[Accession Number]
 Name of Depository Institution: Korean Collection for Type Cultures (KCTC), Korea Research Institute of Bioscience and Biotechnology
 Accession No: KCTC14533BP
 Date of deposit: 20210412

EFFECT OF THE INVENTION

A novel strain of the present disclosure may increase physiological activity by increasing the content of minor ginsenosides among the total ginsenosides through bioconversion of major ginsenosides, and in particular, the novel strain has an excellent efficacy of selectively increasing the content of a specific minor ginsenoside ((R) type ginsenoside Rg3) with high physiological activity, among minor ginsenosides.

Further, a method of preparing a red ginseng fermentation product of the present disclosure may prepare a red ginseng fermentation product showing a selective increase in the content of the (R) type ginsenoside Rg3 and in the (R) type ginsenoside Rg3/(S) type ginsenoside Rg3 value by using the strain.

What is claimed is:

1. A composition comprising a red *ginseng* fermentation product comprising an *Aspergillus oryzae* LGYM4 strain deposited with Accession No. KCTC 1453 3BP or a red *ginseng* fermentation product generated from an *Aspergillus oryzae* LGYM4 strain deposited with Accession No. KCTC 14533BP, wherein the composition is a food composition, a cosmetic composition, a quasi-drug composition, or a pharmaceutical composition, wherein the red *ginseng* fermentation product is in the form of a concentrate, wherein the red *ginseng* fermentation product has an increased content of the (R) type ginsenoside Rg3 as compared to a composition including red *ginseng* before fermentation, and wherein the red *ginseng* fermentation product has a decreased content of the Rg1 and Rd ginsenosides as compared to a composition including red *ginseng* before fermentation.

2. The composition of claim 1, wherein the red *ginseng* fermentation product has an increased value of (R) type ginsenoside Rg3/(S) type ginsenoside Rg3 as compared to a composition including red *ginseng* before fermentation.

3. A method of preparing a red *ginseng* fermentation product, the method comprising the step of performing a fermentation by inoculating an *Aspergillus oryzae* LGYM4 strain deposited with Accession No. KCTC 14533BP into a composition including red *ginseng*,
- wherein the prepared red *ginseng* fermentation product has an increased content of the (R) type ginsenoside Rg3 as compared to a composition including red *ginseng* before fermentation, and
- wherein the prepared red *ginseng* fermentation product has a decreased content of the Rg1 and Rd ginsenosides as compared to a composition including red *ginseng* before fermentation.

4. The method of claim 3, wherein the prepared red *ginseng* fermentation product has an increased value of (R) type ginsenoside Rg3/(S) type ginsenoside Rg3, as compared to a composition including red *ginseng* before fermentation.

5. The method of claim 3, further comprising the step of concentrating the prepared red *ginseng* fermentation product.

6. A composition comprising a red *ginseng* fermentation product prepared according to the preparation method of claim 3, wherein the composition is a food composition, a cosmetic composition, a quasi-drug composition, or a pharmaceutical composition.

7. The composition according to claim 1, comprising the red *ginseng* fermentation product, wherein the red *ginseng* fermentation product concentrate comprises a filtered fermentation broth and an alcohol comprising an adsorbed ginsenosides.

8. The composition of claim 7, wherein the filtered fermentation broth and the alcohol comprising the adsorbed ginsenosides are mixed in a 2:1 ratio.

9. A composition comprising a red *ginseng* fermentation product comprising an *Aspergillus oryzae* LGYM4 strain deposited with Accession No. KCTC 14533BP or a red *ginseng* fermentation product generated from an *Aspergillus oryzae* LGYM4 strain deposited with Accession No. KCTC 14533BP, wherein the composition is a food composition, a cosmetic composition, a quasi-drug composition, or a pharmaceutical composition, wherein the red *ginseng* fermentation product has an increased content of the (R) type ginsenoside Rg3 as compared to a composition including red *ginseng* before fermentation, wherein the red *ginseng* fermentation product has a decreased content of the Rg1 and Rd ginsenosides as compared to a composition including red *ginseng* before fermentation.

\* \* \* \* \*